US006335450B1

(12) United States Patent
Farooqui et al.

(10) Patent No.: US 6,335,450 B1
(45) Date of Patent: Jan. 1, 2002

(54) EFFICIENT CYCLIC-BRIDGED CYANINE DYES

(75) Inventors: Firdous Farooqui, Brea; Maged A. Michael, Placentia; M. Parameswara Reddy, Brea, all of CA (US)

(73) Assignee: Beckman Coulter, Inc., Fullerton, CA (US)

( * ) Notice: Subject to any disclaimer, the term of this patent is extended or adjusted under 35 U.S.C. 154(b) by 0 days.

(21) Appl. No.: 09/710,574

(22) Filed: Nov. 9, 2000

(51) Int. Cl.$^7$ .................... C07D 277/60; C07D 277/62; C07D 209/02; C07D 209/04

(52) U.S. Cl. .................. 548/148; 548/156; 548/465; 548/469; 544/212; 544/83; 544/113; 430/541; 435/6

(58) Field of Search ................. 548/148, 156, 548/465, 469; 544/212, 83, 113; 430/541; 435/6

(56) References Cited

U.S. PATENT DOCUMENTS

| 4,981,977 A | 1/1991 | Southwick et al. ........... 548/55 |
| 5,569,587 A | 10/1996 | Waggoner ...................... 435/6 |
| 5,571,388 A | 11/1996 | Patonay et al. ............. 204/461 |
| 5,627,027 A | 5/1997 | Waggoner ...................... 435/6 |

FOREIGN PATENT DOCUMENTS

| EP | 0 670 374 B1 | 5/1988 |
| EP | 0 753 584 A1 | 1/1997 |

OTHER PUBLICATIONS

G. A. Reynolds, et al., "Stable Heptamethine Pyrylium Dyes that Absorb in the Infrared," J. Org. Chem., vol. 42, No. 5, pp. 885–888, 1977.

Lucjan Strekowski, et al., "Substitution Reactions of a Nucleofugal Group in Heptamethine Cyanine Dyes. Synthesis of an Isothiocyanato Derivative for Labeling of Proteins with a Near–Infrared Chromophore," J. Org. Chem. vol. 57, No. 17, pp. 4578–4589, 1992.

(List continued on next page.)

*Primary Examiner*—Jezia Riley
(74) *Attorney, Agent, or Firm*—William H. May; Arnold Grant; Hogan & Hartson LLP

(57) ABSTRACT

This invention provides cyclic-bridged dyes, particularly cyclic-bridged cyanine dyes, of the general formula:

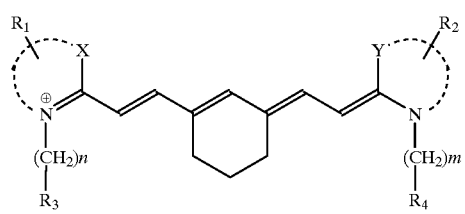

In this formula, each dotted line represents carbon atoms necessary to form a fused substituted or unsubstituted aromatic ring; n=1–18; m=1–18, selected independently from n. X and Y are selected independently from the group consisting of S, O, N, $CH_2$ and $C(CH_3)_2$; at least one of said $R_1$ and $R_2$ comprises a sulfonic acid or sulfonate group attached to the aromatic ring; and $R_3$ and $R_4$ are independently selected from the group consisting of carboxyl, activated carboxyl and methyl, wherein at least one of said $R_3$ and $R_4$ groups is carboxylate or activated carboxylate. Methods of making and using the cyclic-bridged dyes are also provided.

40 Claims, 8 Drawing Sheets

OTHER PUBLICATIONS

Narasimhachir Narayanan, et al., "A New Method for the Synthesis of Heptamethine Cyanine Dyes: Synthesis of New Near–Infrared Fluorescent Labels," J. Org. Chem., vol. 60, No. 8, pp. 2391–2395 (w/additions and corrections page), 1995.

Lucjan Strekowski, et al., "Functionalization of Near–Infrared Cyanine Dyes," J. Heterocyclic Chem., vol. 33, pp. 1685–1688, Nov.–Dec. 1996.

Lucjan Strekowski, et al., "Facile Derivatizations of Heptamethine Cyanine Dyes," Synthetic Communications, 22(17), pp. 2593–2598, 1992.

Yu. L. Slominskii, et al., "Polymethine Dyes with Hydrocarbon Bridges. Enamino Ketones in the Chemistry of Cyanine Dyes," pp. 1854–1860. Institute of Organic Chemistry, Academy of Sciences of the Ukrainian SSR, Kiev. Translated from Zhurnal Organicheskoi Khimii,vol. 19, No. 10, pp. 2134–2142, Oct. 1983. Original article submitted Nov. 22, 1982.

Yu. L. Slominskii, et al.,"Tricarbocyanines with Hydrocarbon Rings in the Chromophore," Journal of Organic Chemistry of the USSR, vol. 19, No. 10, Part 2, pp. 61–64, Oct. 1983.

Narasimhachari Narayanan, et al., "New Year Infrared Dyes for Applications in Bioanalytical Methods," SPIE, vol. 2388, pp. 6–15, Feb. 6–8, 1995.

EFFICIENT CYCLIC-BRIDGED CYANINE DYES

BACKGROUND OF THE INVENTION

1. Area of the Art

The invention relates generally to activated dyes and specifically to activated cyclic-bridged cyanine dyes, their synthesis and methods of use in labeling of biopolymers.

2. Description of the Prior Art

Many procedures employed in biomedical research and recombinant DNA technology rely heavily on the use of nucleotide or polynucleotide derivatives radioactively labeled with isotopes. However, the rapidly increasing costs of radioactive waste disposal, together with an increased awareness of the potentially harmful effects of exposure to radiation, have contributed to a shift of emphasis toward other ways of labeling synthetic oligonucleotides. Although many different types of non-radioactive labels have found their use in biological detection assays, use of fluorescent labels has expanded rapidly in recent years due to both improvements in detection instrumentation and the increased number of novel fluorescent labeling reagents.

The sensitivity and accuracy of fluorescence detection techniques depend on the physical and chemical characteristics of the dyes they employ. A common problem with many commercially available fluorescent labeling reagents is that they are not water-soluble and must be dissolved in organic solvents prior to labeling substrate in aqueous media. Such organic solvents can have a deleterious effect upon sensitive substrates. Another problem related to the dye's chemical structure is non-specific staining of cellular matter by the dye, which reduces signal-to-noise ratio during observation.

Cyanine and related dyes offer many advantages over existing fluorescent labeling reagents, including a high extinction coefficient, relatively high quantum efficiency, ease of chemical manipulation, and reasonable stability to reagents, pH and temperature. Because of a low fluorescence background of biological materials and a high absorbency of cyanine dyes in the longer wavelength portion of the spectrum, cyanine dyes provide excellent signal-to-noise ratios. Certain cyanine and related dyes are relatively photostable and do not rapidly bleach under the fluorescence microscope. They can be covalently attached to biological and non-biological markers to make these materials fluorescent. Additionally, due to their relatively small size, cyanine dyes minimally perturb the function of the labeled product. Finally, the versatility of functional groups that can be incorporated into cyanine dyes permits control over the solubility of the dye and labeled product and helps reduce non-specific binding of the labeled materials to irrelevant components in an assay mixture (Waggoner, U.S. Pat. No. 5,569,587 and U.S. Pat. No. 5,627,027).

In order to improve covalent attachment of cyanine dyes to target molecules, techniques for activating cyanine dyes by the incorporation of a reactive functional group (or activating group) have been developed. Waggoner (U.S. Pat. No. 5,569,587 and U.S. Pat. No. 5,627,027) has presented numerous cyanine dye derivatives that can be used as covalently reacting molecules. The reactive groups used in these dyes are isothiocyanate, isocyanate, monochlorotriazine, dichlorotriazine, mono-or di-halogen substituted pyridine, mono- or di-halogen substituted diazine, aziridine, sulfonyl halide, acid halide (except for fluorides), hydroxysuccinimide ester, hydroxy sulfosuccinimide ester, imido ester, glyoxal and aldehyde. Waggoner has suggested incorporation of carboxylic groups into the basic cyanine structure to increase solubility of the dye in water and to permit fluorescent labeling through the use of derived active esters (U.S. Pat. No. 4,981,977 and U.S. Pat. No. 5,627,027).

Cyanine dyes have a general structure where the chromophore of the cyanine dyes is composed of a series of conjugated double bonds having two quaternary nitrogen atoms at the terminal ends which share one positive charge. According to the number of central double bonds, the cyanine dyes can be classified as monocarbocyanine (also known as trimethinecarbocyanine or Cy3), dicarbocyanine (also known as pentamethinecarbocyanine or Cy5), and tricarbocyanine (also known as heptamethinecarbocyanine or Cy7). The number of central double bonds (referred to hereinafter as k) determines in part the excitation color. Often, higher values of k contribute to increased fluorescence and absorbance. At values of k above 4, however, the compound becomes unstable. Thereupon, further fluorescence can be imparted by modifications at the ring structures. When k=2, the excitation wavelength is about 650 nm and the compound is very fluorescent.

By synthesizing structural modifications of the chromophore portion of cyanine dyes, different fluorescent labeling reagents absorbing and emitting in a broad spectrum range from 400 to nearly 1100 nm can be obtained. For example, U.S. Pat. No. 5,571,388 describes pentamethine and heptamethine cyanine dyes incorporating various cyclic structures within a chain of conjugated double bonds. These dyes absorb light having wavelengths from 630 nm to 900 nm.

Although above-described efforts have increased the number of cyanine dyes suitable for labeling biomolecules, many of these dyes are not especially photostable, and their solubility properties are not optimal for many uses that would involve fluorescence detection of labeled materials. It would be highly desirable to provide stable cyanine dyes having suitable absorption and fluorescence properties and useful linking groups for attachment to biomolecules. It is also desirable to have dyes that can be used with both organic and aqueous solvents.

SUMMARY OF THE INVENTION

We have discovered that dyes having more than two central double bonds (for example, Cy7 dyes) are particularly unstable during storage and manipulation. Accordingly, it is an object of the present invention to provide stable fluorescent dyes with more than two central double bonds and stable Cy7 dyes, in particular. It is also an object of the present invention to provide convenient methods for their synthesis and use in labeling biological and non-biological materials.

These and other objects are achieved in dyes of the present invention having a following general formula:

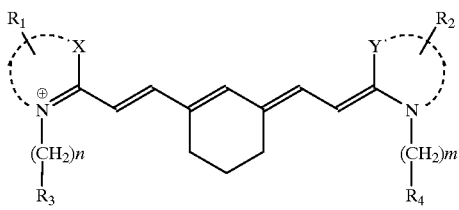

(I)

In this formula, each dotted line represents carbon atoms necessary to form a fused substituted or unsubstituted aromatic ring; n=1–18; and m=1–18, selected independently from n. X and Y are independently selected from the group consisting of S, O, N, $CH_2$ and $C(CH_3)_2$, and at least one of $R_1$ and $R_2$ comprises a sulfonic acid or sulfonate group attached to the aromatic ring. $R_3$ and $R_4$ are independently selected from the group consisting of carboxyl, activated carboxyl and methyl. According to the present invention, it is required that at least one of said $R_3$ and $R_4$ groups is carboxylate or activated carboxylate. In one embodiment, both $R_3$ and $R_4$ are a carboxylate or an activated carboxylate. In another embodiment, either $R_3$ or $R_4$ is carboxylate or activated carboxylate. The activated carboxylate may be an ester, for example an ester of N-hydroxynapthalimide. According to embodiments of the present invention, the dyes may be cyclic-bridged cyanine dyes and, more particularly, cyclic-bridged Cy7-type cyanine dyes.

Another aspect of the present invention provides a method of synthesizing a cyclic-bridged dye. The method includes the steps of:

(a) forming a cyclic-bridged derivative of the dye having a formula:

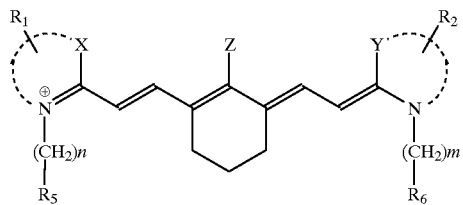

(b) replacing the halogen with a hydrogen.

In the formula (II), each dotted line represents carbon atoms necessary to form a fused substituted or unsubstituted aromatic ring; n=1–18; m=1–18, selected independently from n; and Z is a halogen. X and Y are selected independently from the group consisting of S, O, N, $CH_2$ and $C(CH_3)_2$ and at least one of the $R_1$ and $R_2$ comprises a sulfonic acid or sulfonate group attached to the aromatic ring. $R_5$ and $R_6$ are independently selected from a carboxyl or a methyl, wherein at least one of said $R_5$ and $R_6$ is a carboxyl.

According to embodiments of the present invention, the dye can be a cyanine dye, and particularly Cy7, BCy7, and DBCy7. In one embodiment, both $R_5$ and $R_6$ are carboxyls. In another embodiment, either $R_5$ or $R_6$ is carboxyl. The halogen may be a chlorine.

In one embodiment of the present invention, the step of forming a cyclic-bridged derivative of the dye comprises the steps of:

(a1) mixing Compounds (XI) and (XII) with 2-chloro-1-formyl-3-hydroxymethylene-cyclohexene to form a reaction mixture; and (a2) maintaining the reaction mixture under conditions that allow the formation of the cyclic-bridged derivative of the dye.

Compound (XI) may be any compound having a general formula:

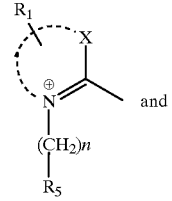 and

Compound (XII) may be any compound having a general formula:

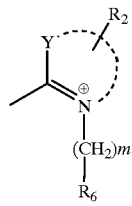

In the formulas of Compounds (XI) and (XII), each dotted line represents carbon atoms necessary to form a fused substituted or unsubstituted aromatic ring; n=1–18; m=1–18, selected independently from n; and X and Y are selected from the group consisting of S, O, N, $CH_2$ and $C(CH_3)_2$. At least one of the groups $R_1$ and $R_2$ comprises a sulfonic acid or sulfonate group attached to the aromatic ring. Groups $R_5$ and $R_6$ are independently selected from a carboxyl or a methyl, wherein at least one of said $R_5$ and $R_6$ is carboxyl.

Another aspect of the present invention provides a method wherein the activated cyclic-bridged dye of this invention is used to label a biological or a non-biological material.

The present invention has been found to provide a number of advantages. By incorporating a cyclic moiety into the chain of conjugated double bonds of Cy7-type dyes, their partial conversion into Cy5-like species is effectively prevented and stable dyes are formed. As a result, a higher overall yield of labeled product is achieved as compared to labeling with unmodified Cy7-type dyes. As explained in greater detail below, N-hydroxynaphthalimide ester of Cyclic DBCy7 was successfully conjugated to amino oligonucleotides and dideoxynucleotides. While cyclic-bridged DBCy7-labeled terminators performed well in sequencing, cyclic-bridged DBCy7-labeled primers produced good results in DNA Fragment Analysis. Many other procedures employed in biomedical research and using fluorescent dyes may also benefit from the dyes of the present invention.

The invention is defined in its fullest scope in the appended claims and is described below in its preferred embodiments.

DESCRIPTION OF THE FIGURES

The above-mentioned and other features of this invention and the manner of obtaining them will become more apparent, and will best be understood, by reference to the following description, taken in conjunction with the accompanying drawings, in which.

DETAILED DESCRIPTION OF THE INVENTION

Figure 1A:
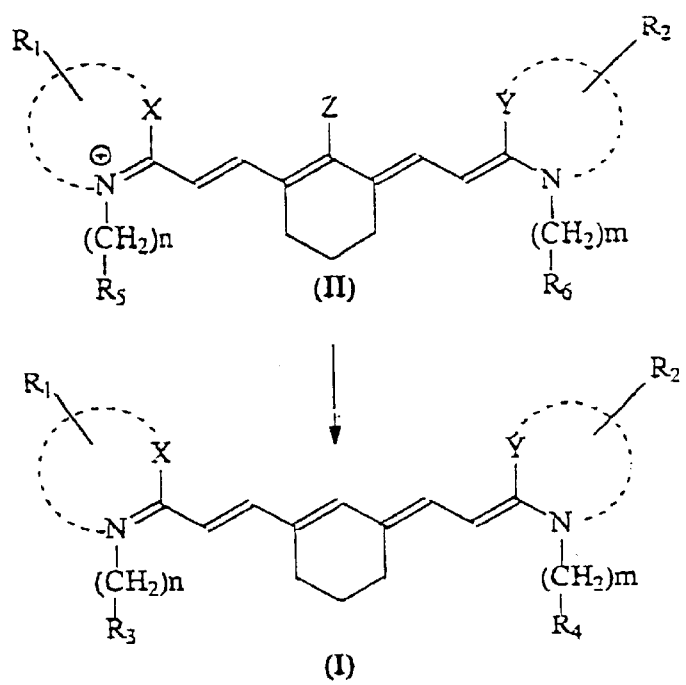
FIGS. 1A and 1B schematically illustrate a method of synthesis of a cyclic-bridged dye of the present invention.

The present invention provides a cyclic-bridged dye having a general formula:

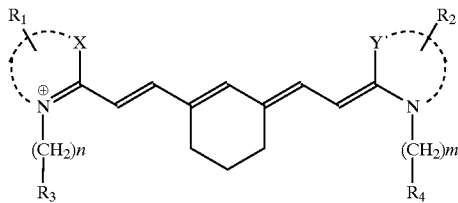

(I)

In this formula, each dotted line represents carbon atoms necessary to form a fused substituted or unsubstituted aromatic ring, and X and Y are selected independently from the group consisting of S, O, N, $CH_2$ and $C(CH_3)_2$. The length of the attached alkyl chain is preferably about 1 to 18 carbon atoms long (n and m are in the range from 1 to 18, selected independently). The most practical alkyl chain length is about 6 carbon atoms long. In one embodiment, n is 5 and m is 1.

The substituted or unsubstituted aromatic ring may be a heterocyclic ring, a single ring aromatic structure such as a phenyl ring, or a fused ring structure such as a naphthyl ring. The absorption and emission wavelengths of the dye are not restricted to a particular region of the spectrum but may be anywhere from the near UV through the near IR region or beyond these extremes.

Many dye molecules, and particularly cyanine dye molecules, tend to form aggregates in aqueous solution, particularly when inorganic salts are present, as in buffered solutions and physiological salines. These aggregates usually have absorption bands shifted to the short wavelength side of the monomer absorption and, generally, have a weak fluorescence. It has been found that the arylsulfonate dyes with a sulfonate group attached to an aromatic ring structure of the dye have a minimal tendency to form these aggregates. The sulfonate groups attached to an aromatic ring structure of the dyes have little or no effect on the chromophore, but do increase the photostability, water solubility and charge density of the molecules. The term sulfonate is meant to include sulfonic acid, because the sulfonate group is merely ionized sulfonic acid. Consequently, for the purposes of increasing water solubility, it is required that at least one of the $R_1$ and $R_2$ groups is a sulfonic acid or a sulfonate group attached to the aromatic ring. In order to reduce unwanted nonspecific binding or interaction between two or more reactive chromophores, a non-sulfonate $R_1$ or $R_2$ group can be selected from the well-known polar and electrically charged chemical groups, such as phosphate, phosphonate, nitrate.

According to this invention, $R_3$ and $R_4$ may be independently selected from the group consisting of carboxyl, activated carboxyl and methyl. For the purpose of this invention, an activated carboxyl is a carboxyl derivative having a reactive functional group which permits covalent attachment of the dye to any biological or nonbiological molecule of the present invention. While it is required that at least one $R_3$ or $R_4$ group is a carboxylate or an activated carboxylate (monofunctional species), both $R_3$ and $R_4$ groups may be carboxylates or activated carboxylates (bifunctional species). Examples of such activated carboxylates include, but are not limited to, esters of N-hydroxynapthalimide, N-hydroxysuccinimide, N-hydroxyphthalimide and sulfo-N-hydroxysuccinimide. In one embodiment, activated carboxylate is an ester of N-hydroxynapthalimide.

It is a discovery of the present invention that long stretches of conjugated double bonds may cause instability of the dye during its storage and manipulation. It is also a discovery of the present invention that a cyclic structure incorporated within the conjugated double bonds may stabilize such dyes. Consequently, the dyes of the present invention incorporate a stabilizing cyclic structure within their conjugated double bonds. According to one embodiment of the present invention, the cyclic structure is:

According to embodiments of the present invention, the dyes may be cyanine dyes. Cyanine dyes have several desirable properties to serve as sensitive detection labels, including absorption at longer wavelengths (which translates into the use of inexpensive detection systems and low background from biological samples at these wavelengths), high extinction coefficient, relatively high quantum efficiency, small molecular size, ease of chemical manipulation without compromising the fluorescence characteristics, and reasonable stability to reagents, pH and temperature In one embodiment of this invention, cyclic-bridged dyes are cyclic derivatives of tricarbocyanine dyes. Examples of the dyes include, but are not limited to Cy7, BCy7 and DBCy7. The benzoindole cyanine dye (BCy7) has one benzene group substitution and dibenz Cy7 (DBCy7) has two extra benzene group substitutions relative to the corresponding indole cyanine Cy7. As such, benzoindole cyanines have absorption and emission maxima longer than their indole counterpart. Cy7 is commercially available from Amersham and BDL. Alternatively, cyanine dyes can be synthesized de novo, as previously described (R. J. Mujumder et al., *Bioconjugate Chemistry*, 4(2):105 (1993); and S. R. Mujumder et al., *Bioconjugate Chemistry*, 7(2):356 (1996); both of which are incorporated herein by reference).

Another aspect of the present invention provides a method of synthesizing a cyclic-bridged dye. The general synthetic scheme for the preparation of a cyclic-bridged dye of the present invention is shown in FIG. 1A. The method includes the steps of:

(a) forming a cyclic-bridged derivative of the dye having a formula:

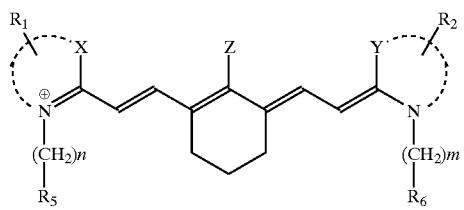

(II)

(b) replacing the halogen with a hydrogen.

In the formula (II), each dotted line represents carbon atoms necessary to form a fused substituted or unsubstituted aromatic ring; n=1–18; m=1–18, selected independently from n; X and Y are selected independently from the group consisting of S, O, N, $CH_2$ and $C(CH_3)_2$; and Z is a halogen. At least one of the $R_1$ and $R_2$ comprises a sulfonic acid or sulfonate group attached to the aromatic ring. $R_5$ and $R_6$ are independently selected a carboxyl or a methyl, wherein at least one of said $R_5$ and $R_6$ is carboxyl. In one embodiment, the halogen is chlorine.

The dyes can contain a heterocyclic ring, a single ring aromatic structure such as a phenyl ring, or a fused ring structure such as a naphthyl ring. Preferably, the dyes are the cyanine dyes discussed above, including Cy7, BCy7 and DBCy7.

The cyclic-bridged derivative of the dye (II) may be reacted with a suitable reagent under conditions that are sufficient to replace the halogen Z with hydrogen and to form a cyclic-bridged dye (I). For the purpose of the present invention, suitable reagents are reagents that can react with the halogen Z and replace it with hydrogen. In one embodiment of the present invention, the reagent is a mixture of sodium ethanethiolate ($NaSC_2H_5$), ethane thiol and dimethylformamide (DMF). Other reagents, such as $PhSNa/Ph_2PH$, may also be used. For the purpose of the present invention, sufficient conditions are any conditions which allow replacement of the halogen Z with hydrogen. In accordance with one embodiment, the reaction may be carried out at about 100° C. under a nitrogen atmosphere.

Figure 1B:
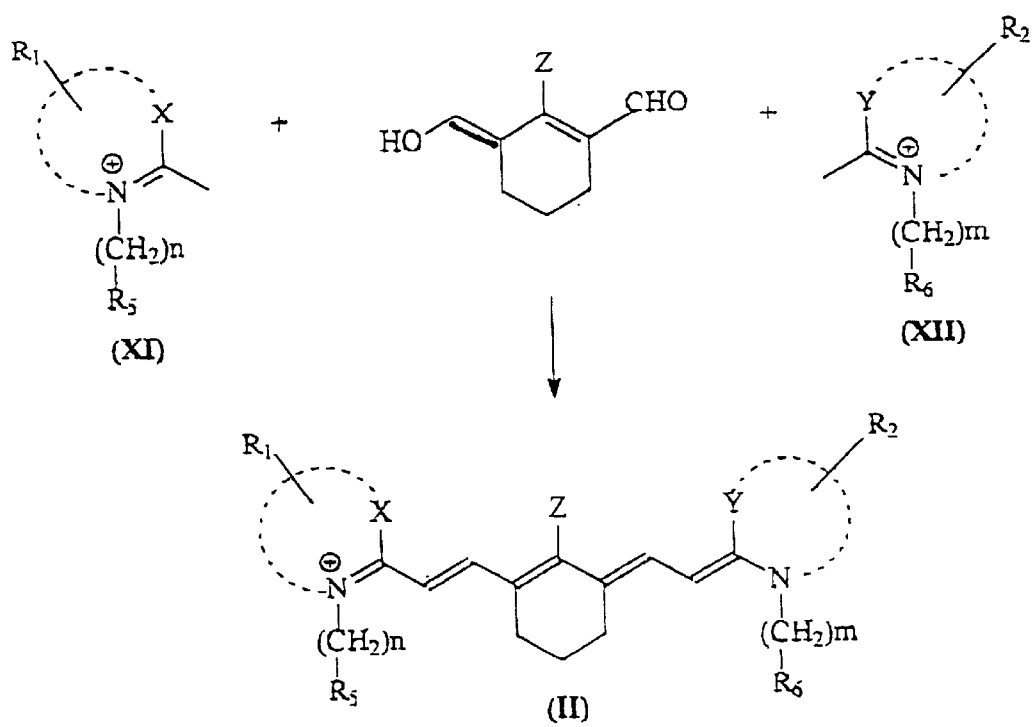

In accordance with one embodiment of the present invention and as depicted in FIG. 1B, the step (a) of forming a cyclic-bridged derivative of the dye may comprise:

(a1) mixing Compounds (XI) and (XII) with 2-chloro-1-formyl-3-hydroxymethylene-cyclohexene to form a reaction mixture; and (a2) maintaining the reaction mixture under conditions that allow the formation of the cyclic-bridged derivative of the dye.

Compound (XI) may be any compound having a general formula:

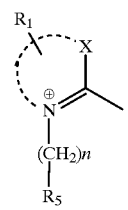

Compound (XII) may be any compound having a general formula:

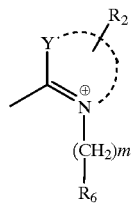

In the above formulas dotted lines represent carbon atoms necessary to form a fused substituted or unsubstituted aromatic ring. In the above formulas, n=1–18; m=1–18, selected independently from n; X and Y are selected independently from the group consisting of S, O, N, $CH_2$ and $C(CH_3)_2$; at least one of the $R_1$ and $R_2$ comprises a sulfonic acid or sulfonate group attached to the aromatic ring; and $R_5$ and $R_6$ are independently selected from a group consisting of a carboxyl and a methyl, wherein at least one of said $R_5$ and $R_6$ is carboxyl.

Figure 1C:
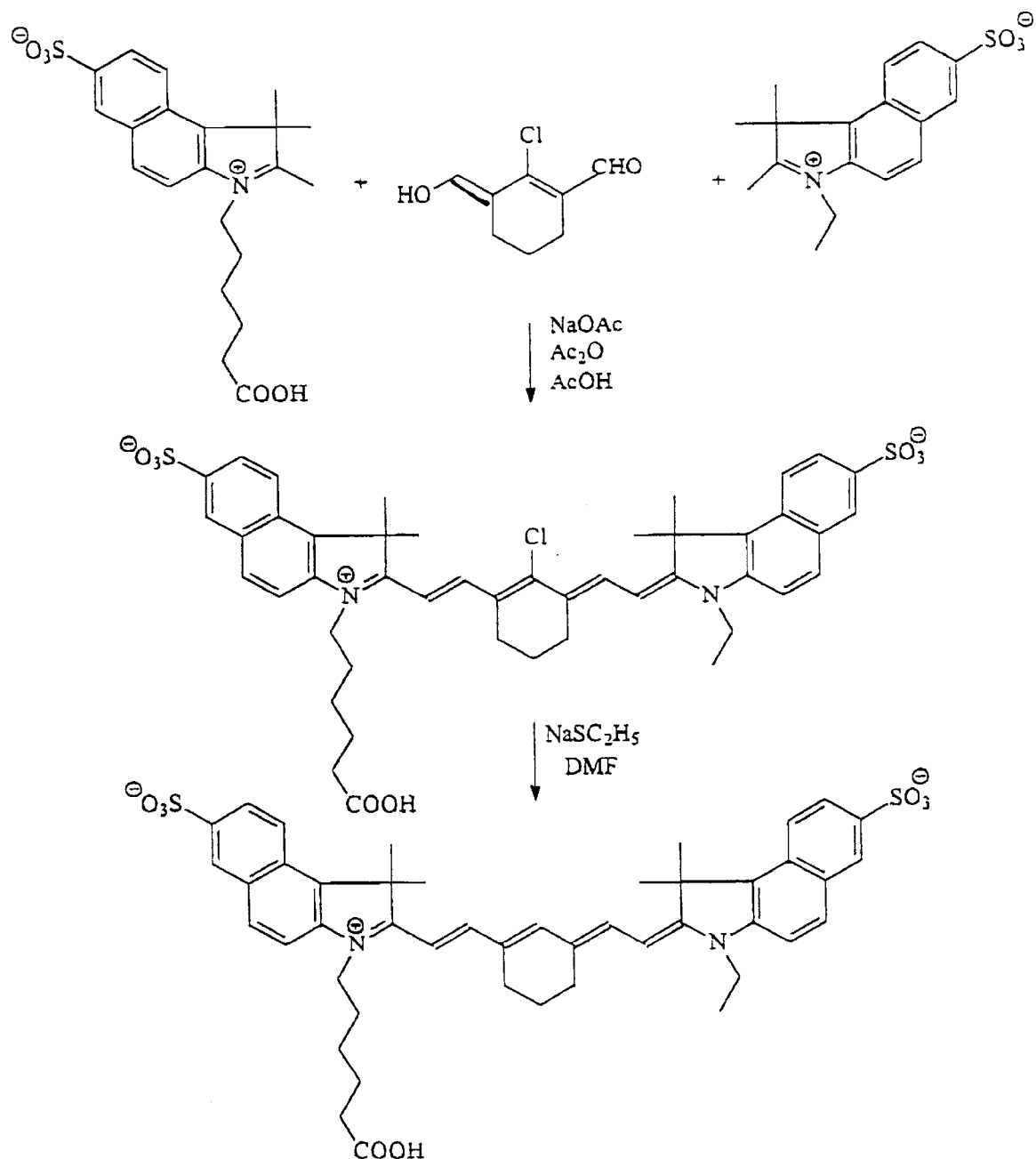
FIG. 1C shows a reaction scheme, illustrating synthesis of cyclic DBCy7 monofunctional carboxylic acid of the present invention.
Figure 1D:
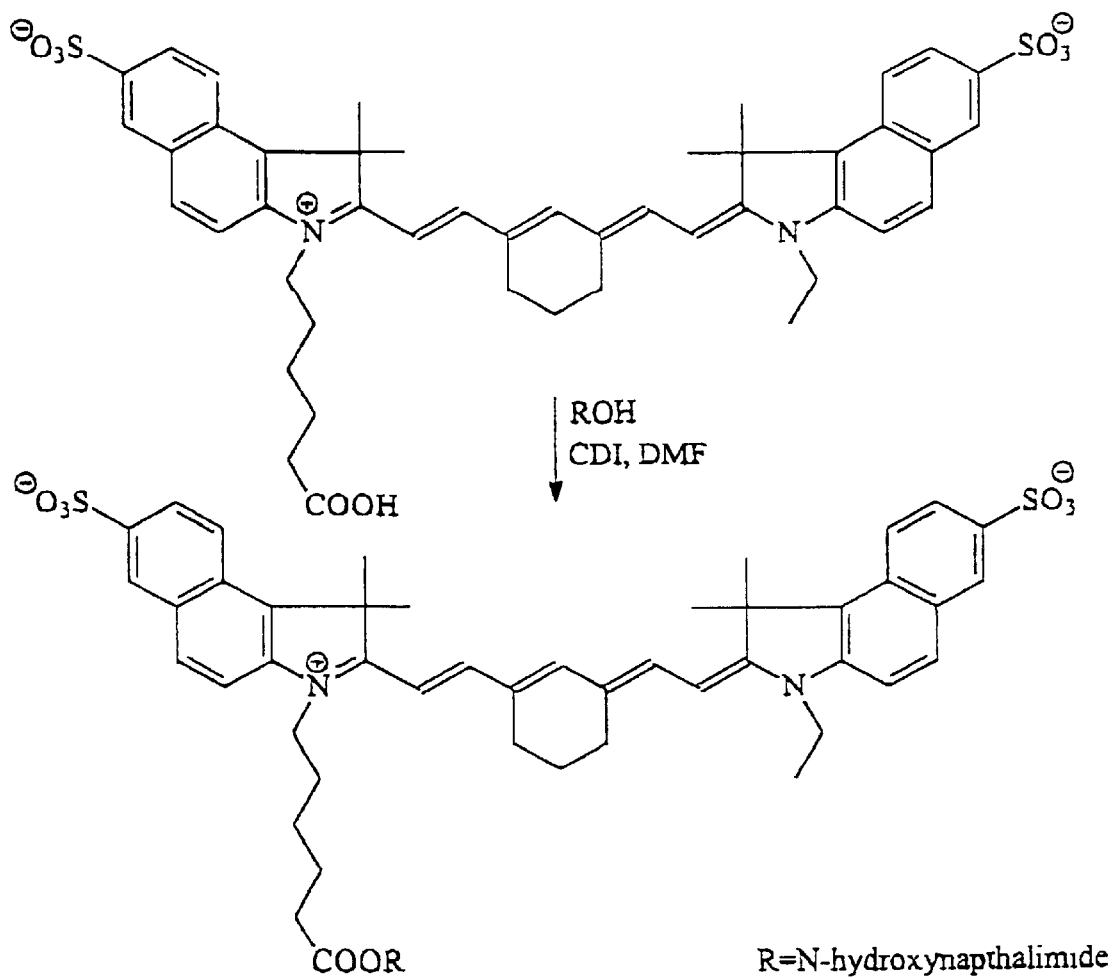
FIG. 1D shows a reaction scheme, illustrating synthesis of active ester of cyclic DBCy7 of the present invention.

The choice of particular Compounds (XI) and (XII) depends on the type of the cyclic-bridged dye to be synthesized. For example, in order to synthesize cyclic DBCy7, benzindole Compounds (XI) and (XIII) may be employed (FIGS. 1C and 1D). To synthesize cyclic Cy7, indole Compounds (XI) and (XIII) may be used. Those skilled in the art will appreciate that other cyclic-bridged dyes may be synthesized by choosing the appropriate compounds (XI) and (XII).

While any compounds with general formulas (XI) and (XIII) may be used according to the method shown in FIG. 1B, in one embodiment Compound (XI) is 1-(5-carboxypentyl)-1, 1, 2-trimethyl-(3H)-indolenium-7-sulfonate and Compound (XII) is 3-ethyl-1, 1, 2-trimethyl-(3H)-indolenium-7-sulfonate. In this embodiment, unsubstituted cyclic dye, cyclic Cy7, is obtained. In another embodiment, Compound (XI) is 1-(5-carboxypentyl)-1, 1, 2-trimethylbenz(e)-indolenium-7-sulfonate and Compound (XII) is 3-ethyl-1, 1, 2-trimethylbenz(e)indolenium-7-sulfonate (FIG. 1C). In this embodiment, a benzene-substituted cyanine dye, cyclic DBCy7, is synthesized. By using only 1-(5-carboxypentyl)-1, 1, 2-trimethyl benz(e) indolenium-7-sulfonate and not 3-ethyl-1, 1, 2-trimethylbenz(e)indolenium-7-sulfonate, one can obtain a bifunctional acid.

For the purpose of this invention, the reaction mixture is maintained under conditions that allow the formation of the cyclic-bridged derivative of the dye (II) with at least one carboxylic group. In one embodiment, the reaction mixture is heated in a solution of sodium acetate in a combination of acetic acid and acetic anhydride to about 120° C. The reaction mixture is incubated at this temperature for about one hour. The resulting intermediate is evaporated to dryness and washed three times with 50 ml of diethyl ether. While different molar ratios of acetic acid and the combination of acetic acid and acetic anhydride may be used, in one embodiment the ratio is about 1:1. According to another embodiment of this invention, molar concentrations of Compounds (XI) and (XII), 2-chloro-1-formyl-3-hydroxymethylene-cyclohexene, sodium acetate and the combination of acetic acid and acetic anhydride are equal. Advantageously, we have discovered that these reaction conditions allow synthesis of the desired product without unwanted side products. For the purpose of this invention, other reaction conditions may also be used as long as they support the formation of the cyclic-bridged derivative of the dye (II) and they do not generate unwanted side products.

In one embodiment, the method for synthesizing a cyclic-bridged derivative of the dye further comprises an additional step of activating the cyclic-bridged dye. This step may be carried out by reacting the cyclic-bridged dye with an activating reagent under a condition sufficient to replace the hydrogen of the carboxyl with a reactive group. For the purpose of this invention, a reactive group is a group capable of forming a covalent bond with a biological or nonbiological molecule (target). An activating reagent is a reagent that provides a reactive group to the dye. Different reactive groups, such as phosphate, phosphonate and nitrate, may be introduced into cyclic-bridged dyes of this invention. In one embodiment, the reactive group is an ester of N-hydroxynapthalimide. Correspondingly, various activating agents, such as phosphate, phosphonate and nitrate, may be used. In one embodiment of the present invention, an activating agent is N-hydroxynapthalimide.

A successful activation of a cyclic-bridged dye depends on reaction conditions. A condition is sufficient if it allows the formation of the activated cyclic-bridged dye. In one embodiment, the dye is dissolved in a solvent prior to reacting with an activating reagent and reaction proceeds at room temperature under nitrogen atmosphere. A mixture of DMF containing 1,1'-carbonyldimidazole may be used as a solvent for the dye. The Example 2 provides further details on suitable reaction conditions. Other reaction conditions may also be used as long as they support formation of the activated cyclic-bridged dye.

(a) providing a biological or a non-biological material having an amino group or a third group or a hydroxyl group; and (b) reacting the activated cyclic-bridged dye of claim 1 with the material under a condition sufficient to couple the dye to the material.

For the purpose of the present invention, materials suitable for labeling may be biological or non-biological materials having functional groups that may react with the dyes of the present invention to form a covalent bond. Examples of such functional groups include, but are not limited to, nitrogen nucleophiles, an amino group or a thiol group or a hydroxyl group. Examples of biological materials include, but are not limited to, cells, proteins, amino-modified nucleic acids, haptens, carbohydrates, dideoxynucleoside terminators, and their combinations. Examples of non-biological materials include, but are not limited to, polymers and polymeric particles that contain nitrogen nucleophiles.

In one embodiment, the amino-modified biological materials are amino-modified biopolymers, e.g. amino-modified oligonucleotides and peptides. The amino-modified oligonucleotides are prepared by attaching a primary aliphatic amine to the 5' terminus of an oligonucleotide. Reagents and instructions for their use in attaching primary aliphatic amine to oligonucleotides are commercially available from Clontech Laboratories, Inc. of Palo Alto, Calif. (See Clontech Product Protocol, PR71095 "N-MMT-$C_n$-AminoModifiers".)

Those skilled in the art will appreciate that any number of sites on the oligonucleotide, in addition to its 5' end phosphate, can be selected to attach the amino group, including the base sites on the sugar moieties. Amino-derivatized biopolymers provide an advantage of favorable reaction kinetics associated with the amide bond formation.

In accordance with embodiments of the present invention, an activated cyclic-bridged dye may be reacted with a biological or non-biological material under conditions sufficient to covalently bind (or couple) the dye to the material. A condition is sufficient if it supports the covalent binding of the dye to the material. In one embodiment, the dye is dissolved in DMF and mixed with an oligonucleotide. The reaction mixture is maintained at room temperature for about 12 hours in the dark. In another embodiment, a dideoxynucleoside terminator and cyclic DBCy7-active ester are dissolved in DMF and diisopropylamine. The reaction proceeds at room temperature for about 12 hours in the dark. Other reaction conditions may also be used, as long as they are sufficient to allow coupling of the dye with the biological or non-biological materials. A buffer, in which the labeling reaction occurs, may be an aqueous buffer, for example, a bicarbonate buffer. In one embodiment of the present invention, a 0.1M bicarbonate buffer (pH 9.0) is used.

The labeled fragments of DNA or RNA can be used as fluorescent hydridization probes to identify the presence and quantity of specific complementary nucleotide sequences in samples containing DNA or RNA. Also, the dye can be attached to a hormone or ligand (such as a hormone, protein, peptide, lymphokine or metabolite), which in turn can be attached to a receptor. When the target is a type of cell, the present invention can be employed to measure the amount of labeled antibodies, which are attached to that type of cell. The measurement can be made by determining the relative brightness or dimness of the luminescence of the cells. Detailed descriptions of these and many other possible applications of cyanine dye labels are provided in the pending U.S. application Ser. No. 09/100,150, entitled "Efficient Activated Cyanine Dyes;" U.S. Pat. No. 5,627,027, entitled "Cyanine Dyes as Labeling Reagents for Detection of Biological and Other Materials by Luminescence Methods;" U.S. Pat. No. 5,569,587, entitled "Method for Labeling and Detecting Materials Employing Luminescent Arylsulfonate Cyanine Dyes;" the relevant contents of which are incorporated herein by reference.

The following examples are intended to illustrate, but not to limit, the scope of the invention. While such examples are typical of those that might be used, other procedures known to those skilled in the art may alternatively be utilized. Indeed, those of ordinary skill in the art can readily envision and produce further embodiments, based on the teachings herein, without undue experimentation.

EXAMPLE 1

Synthesis of Cyclic-Bridged DBCy7 Dye

Activated Cyclic-bridged DBCy7 monoacid dye was synthesized, as depicted in FIG. 1C.

A mixture of 3-ethyl-1, 1, 2-trimethylbenz(e)indolenium-7-sulfonate (951 mg, 3 mmole), 1-(5-carboxypentyl)-1, 1, 2-trimethyl benz(e)indolenium-7-sulfonate (1.2 g, 3mmole), 2-chloro-1-formyl-3-hydroxymethylenecyclohexene (518 mg, 3 mmole) and sodium acetate (246 mg, 3 mmole) in a combination of acetic acid and acetic anhydride (48 ml/27 ml) was heated with stirring at 115–120° C. for one hour. The reaction mixture was cooled to room temperature and solvents were evaporated to dryness. The residue was washed three times with diethyl ether (total of 75 ml) and purified on a silica gel column, using a gradient of $CH_2Cl_2$/MeOH (up to 40% MeOH in $CH_2Cl_2$). The obtained fractions were evaporated to yield 620 mg (24% yield) of the chloro-cyclic DBCy7 monoacid.

Figure 2:
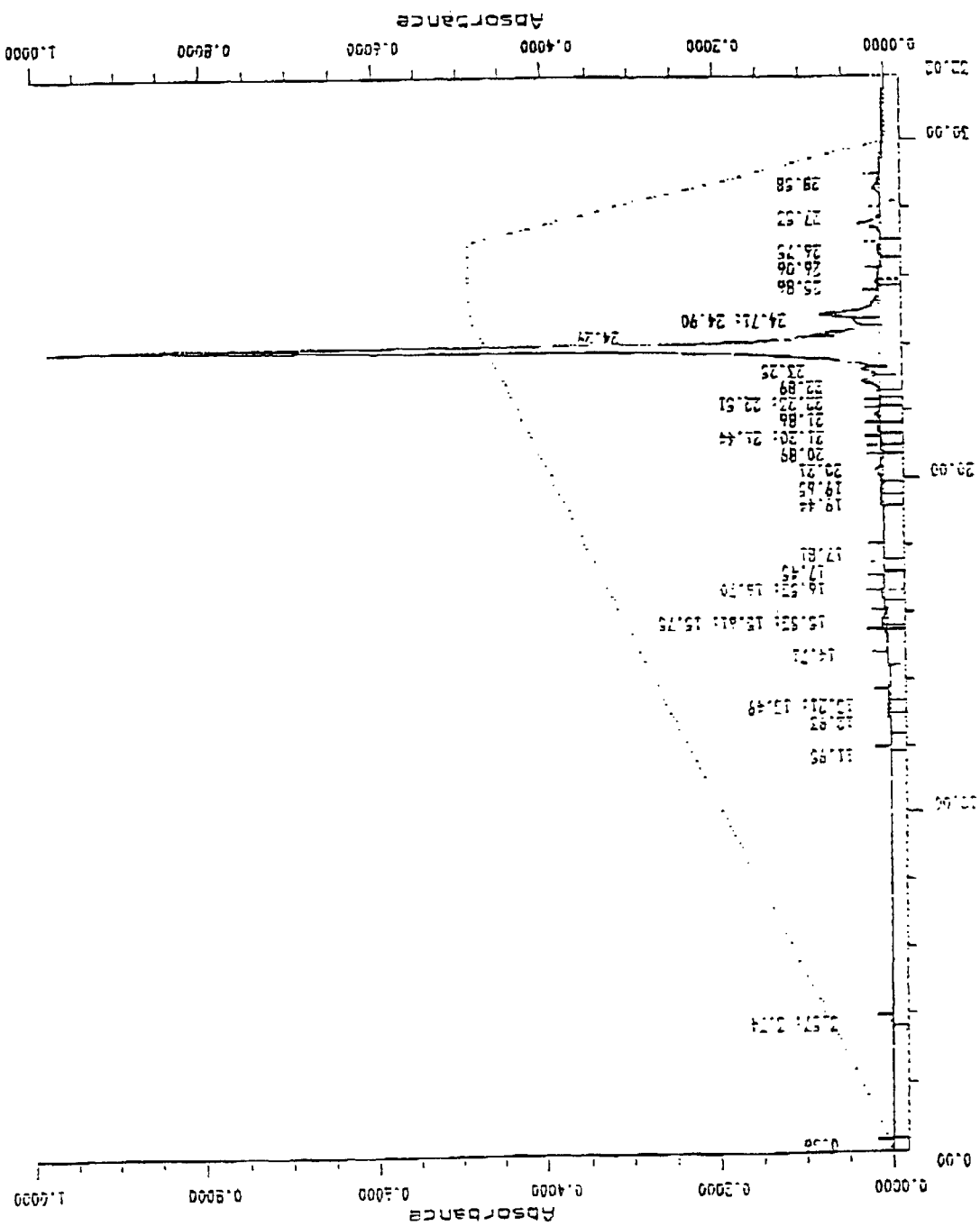
FIG. 2 shows a reverse phase HPLC chromatogram of cyclic chloro-DBCy7 carboxylic monoacid of the present invention.

The purity of the product was analyzed with an HPLC and was found to be 82% (FIG. 2). $^1$H NMR spectra (DMSO-d6) of chloro-cyclic-DBCy7 monoacid was as follows (the chemical shifts are in ppm): 1.14 (q, 3H, CH2-CH3), 1.4–1.5 (m, 6H, 3CH2), 1.89 (s, 12H, (CH3)4, 2.16 (m, 2H, CH2), 2.75 (m, 4H), 4.3 (4H, 2CH2-N), 6.3 (dd, 2H, α, α'-bridge protons), 7.6–8.27 (m, 10H, aromatic protons), 8.4 (dd, 2H, β, β'-bridge protons).

Figure 3:
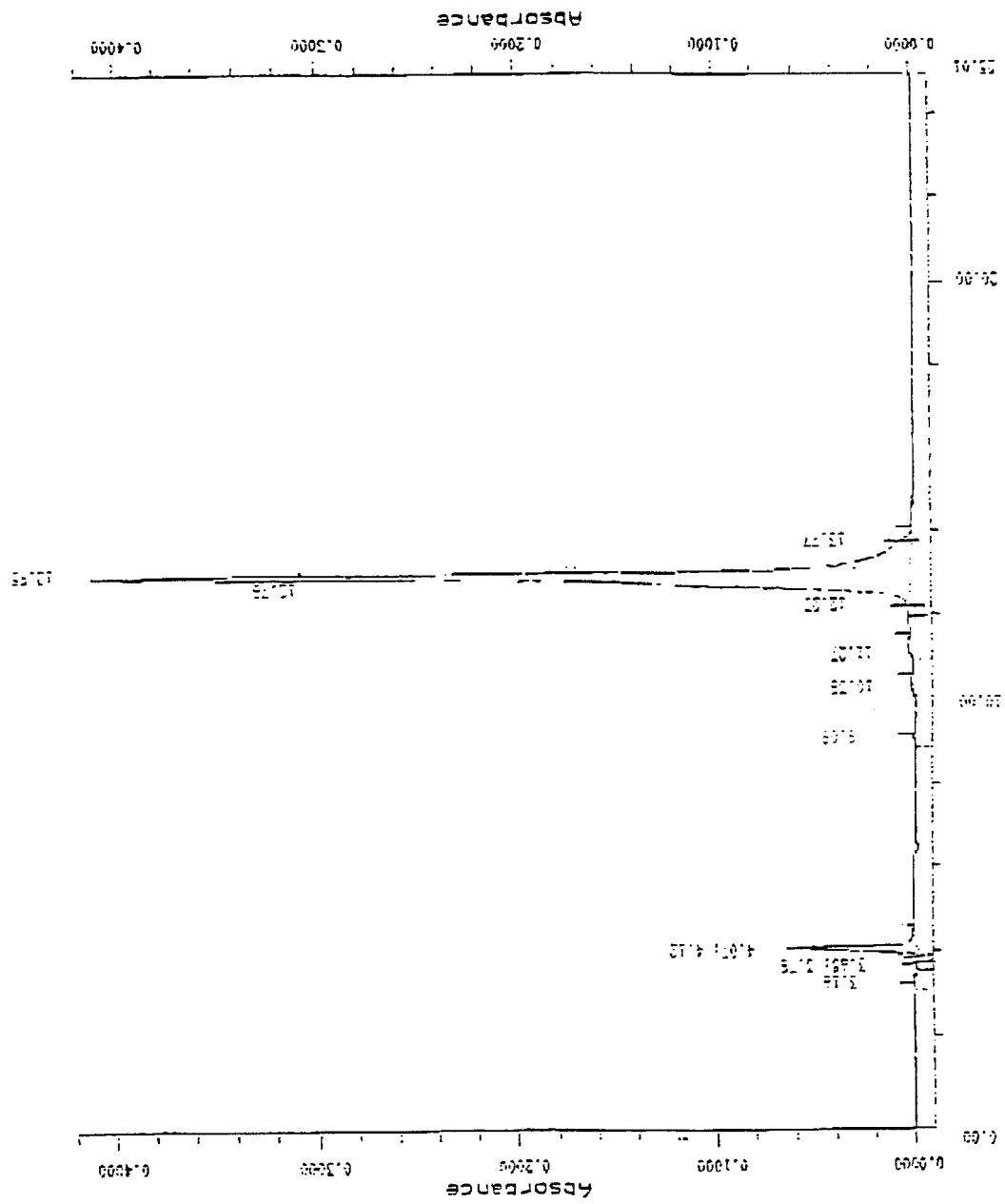
FIG. 3 shows a reverse phase HPLC chromatogram of cyclic DBCy7 carboxylic monoacid of the present invention.

Chloro-cyclic-DBCy7 monoacid (400 mg, 0.466 mmole) was dissolved in 50 ml anhydrous DMF. The solution was added to a mixture of sodium ethanethiolate (0.7856 g, 9.339 mmole) and ethane thiol (778 μl, 10.5 mmole), and incubated at 100° C. for 2 hours under a nitrogen atmosphere. The reaction progress was monitored by UV-NIR absorption changes for aliquots diluted with methanol. A disappearance of the peak at 822 nm and an appearance of the peak at 786 nm of the product were observed. The reaction mixture was cooled to room temperature and saturated with $CO_2$ (dry ice). The solvents were evaporated to dryness under reduced pressure. The residual precipitate was washed twice with ethylacetate (total 40 ml), three times with $CH_2Cl_2$ (total 60 ml), and purified by a reverse phase HPLC. The resulting yield was 18% (68 mg). The product was 90% pure (FIG. 3).

EXAMPLE 2

Activating Cyclic-Bridged DBCy7 Dye (Synthesis of Cyclic-Bridged DBCy7-Monoacid Ester)

Figure 4:
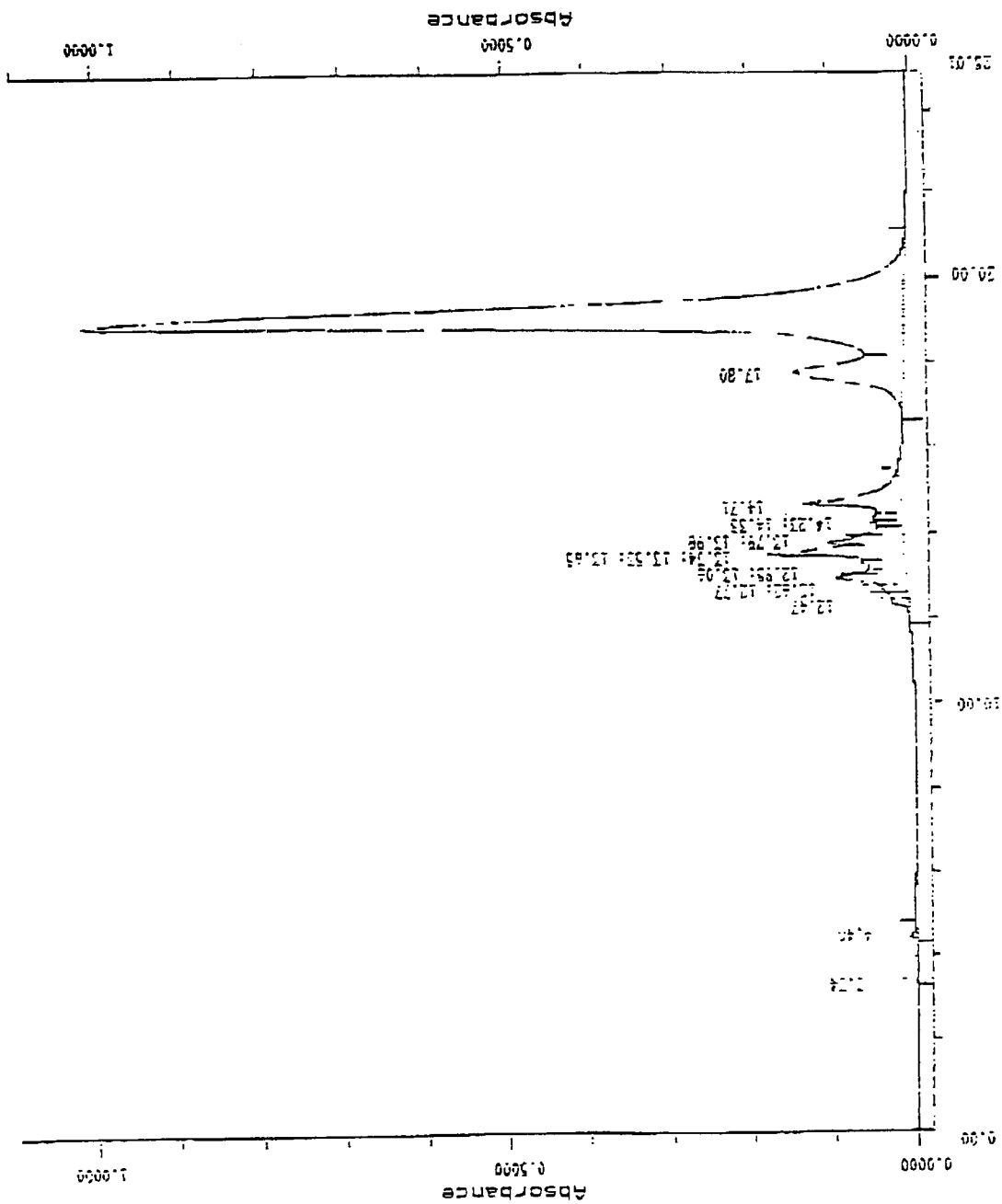
FIG. 4 depicts a reverse phase HPLC chromatogram of cyclic chloro-DBCy7 active ester of the present invention.

Cyclic-bridged DBCy7 monoacid (20 mg, 0.0243 mmole) was dissolved in dry DMF (500 μl) and mixed with 1,1'-carbonyldiimidazole (7.88 mg, 0.0486 mmole). The mixture was stirred at room temperature for 5 hr. under nitrogen atmosphere. N-hydroxynaphthalimide (10.36 mg, 0.0486 mmole) was added and the reaction mixture was stirred overnight (about 16 hrs.) at ambient temperature. After the incubation, the reaction mixture was poured into ethylacetate to precipitate the product. The precipitate was washed once with ethylacetate (1 ml) and twice with ether (total of 2 ml), and dried under vacuum to yield 24 mg (97% yield) of the active ester. The product was analyzed with an HPLC and was found to be 74% pure (FIG. 4).

EXAMPLE 3

Labeling of Oligonucleotides with Cyclic-Bridged DBCy7-Monoacid Ester)

Figure 5:
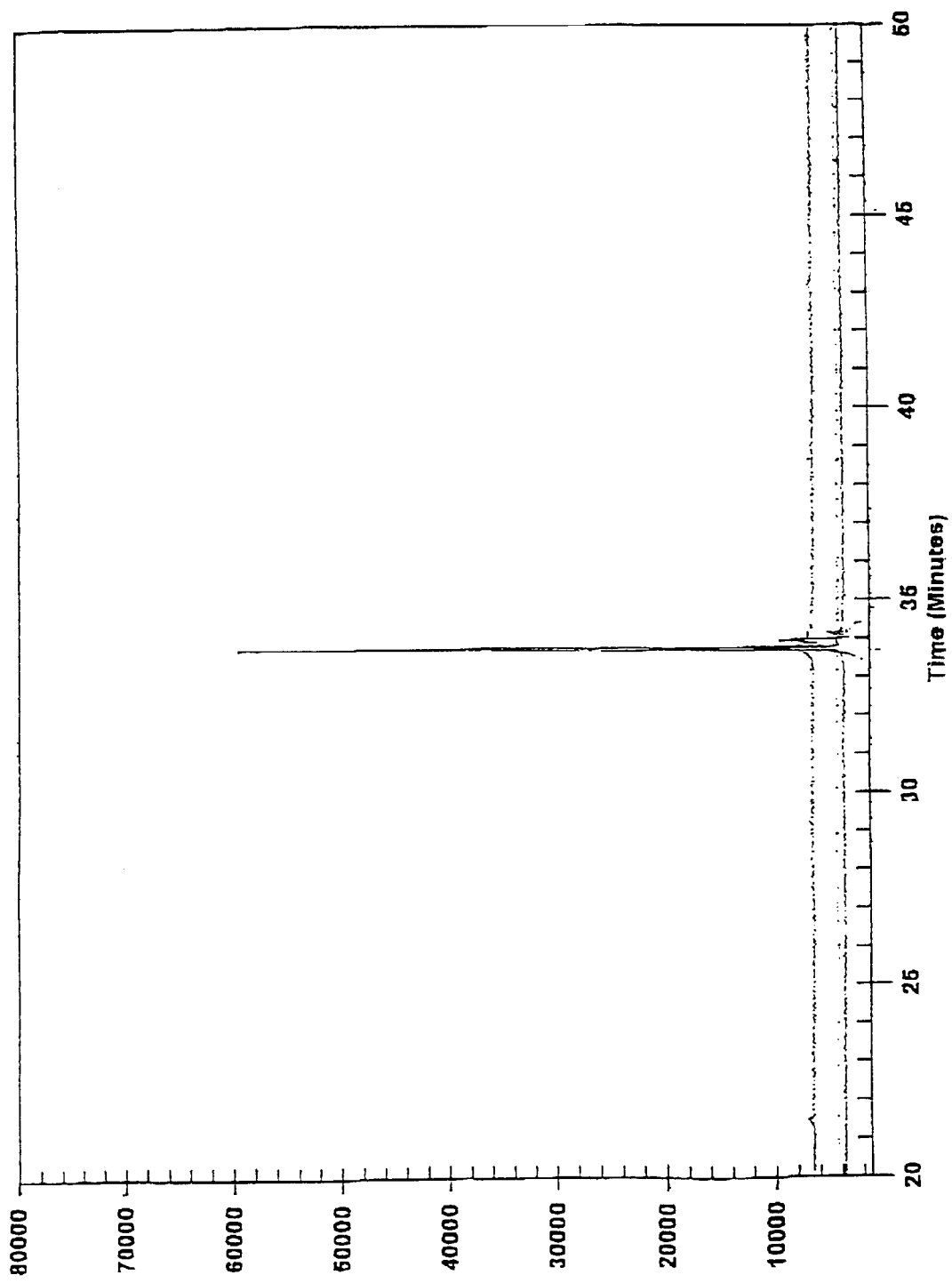
FIG. 5 shows an electropherogram of cyclic-DBCy7-labeled primer obtained with a CEQ 2000 Automated DNA Sequencing System (Beckman Coulter, Inc., Fullerton, Calif.)

An oligonucleotide sequence was synthesized, according to conventional protocols, on oligo 1000M (Beckman) or ABI 392 (Perkin Elmer). A 5'-amino modifier C6 (10-1906-90, Glen research, USA) was incubated with the oligonucleotide for 10 minutes on the instrument at 25° C. After the incubation, the cycle was completed. Mono methoxy trityl (MMT) was removed from the amino modifier and the coupling efficiency was measured. The oligonucleotide was cleaved and deprotected, using ammonia/methyl amine AMA (1/9). The synthesized oligonucleotide was analyzed by capillary electrophoresis (CE) and a reverse phase HPLC, and was found to be 80% pure. The oligonucleotide was coevaporated to dryness with 250 μl of triethylammoniumbicarbonate buffer (pH 8.2–8.6), and then with 250 μl of deionized water. The oligonucleotide was dissolved in 50 μl of 0.1M bicarbonate buffer (pH 9.0). Activated cyclic-bridged DBCy7 dye (3 mg) was dissolved in 50 μl of dry DMF. The oligonucleotide and the dye solutions were mixed together, and 10 μl of diisopropylamine or 10 μl of triethylamine was added to the mixture. The reaction mixture was incubated overnight at room temperature in the dark. The obtained product was purified on a NAP-25 column (Sephadex G-25, Pharmacia, USA), using 0.01M $NH_4OAc$ buffer (pH 7.0). The obtained solution was evaporated to dryness. The dry residue was dissolved in about 200 μl of water and was further purified, using a semiprep C18 RP HPLC column. The purification was carried out using a buffer gradient of Buffer B (100% AcCN) in Buffer A (0.1 M $NH_4$ OAc buffer (pH 7.0). The obtained gradient was as follows: 0–25 min gradient to 50% B, 25–27 min at 50% B, 27–32 min 0% B. The elute from the HPLC was evaporated completely to dryness. The obtained, labeled oligonucleotide was dissolved in water and analyzed with a UV-spectrometer (λ=260 nm), PACE 5000 (Beckman CE), CE-LIF (FIG. 5), and Beckman Gold System HPLC. The obtained product was concluded to be the covalently-labeled cyclic-bridged DBCy7-CONH-oligonucleotide product.

EXAMPLE 4

Labeling of Dideoxynucleoside Terminators with Cyclic-Bridged DBCy7-Monoacid Ester)

Figure 6:
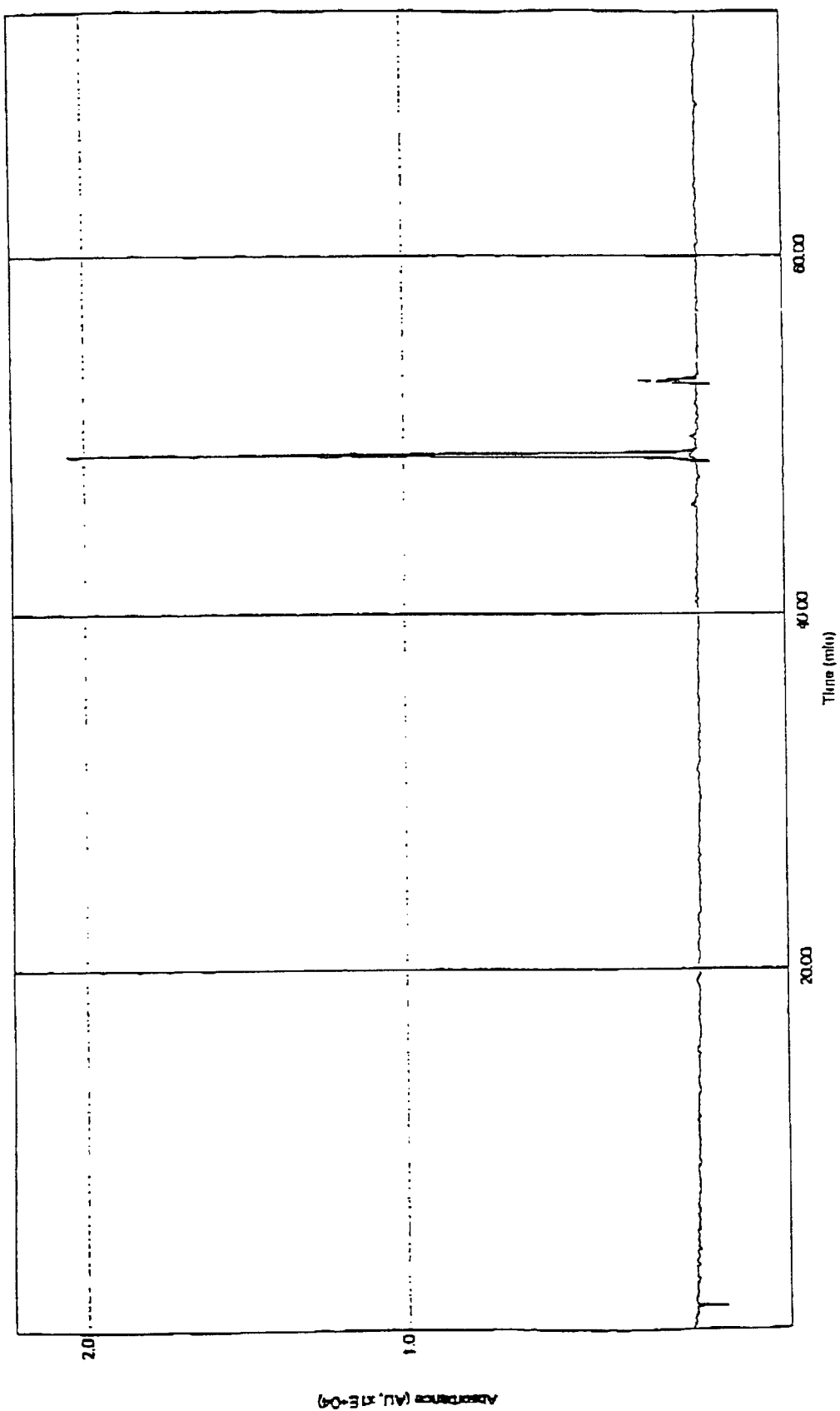
FIG. 6 shows an electropherogram of cyclic-DBCy7-labeled dideoxyadenosine triphosphate obtained with a CEQ 2000 Automated DNA Sequencing System (Beckman Coulter, Inc., Fullerton, Calif.).

A tributylamine salt of 7-(3-amino-1-propynyl)-2', 3'-dideoxyadenosine 5'-triphosphate (2.5 μmole ) was dissolved in 250 μl of DMF. Cyclic-bridged DBCy7-active ester (9 mg) was dissolved in 50 μl of DMF and 15 μl of diisopropylamine. The mixture was mixed well and left overnight in the dark. The obtained product was purified on a semiprep C18 reverse phase HPLC Buffer B: 100% AcCN and Buffer A: 0.1 M $NH_4$ OAc buffer (pH 7.0), initial 80%, 20% B. 0–25 min gradient to 40% B, 25–27 min gradient to 70% B, 27–29 at 70% B, 29–32 min 20% B. The obtained, labeled terminator was analyzed by CE (CEQ 2000, Beckman-Coulter, Calif.) (FIG. 6). The yield of the labeled terminator was found to be about 20–25%.

What is claimed is:

1. An activated cyclic-bridged dye having a formula:

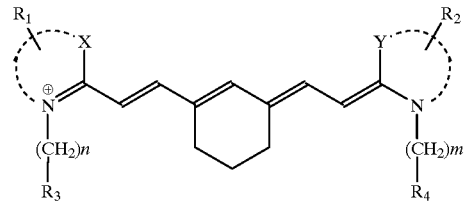

wherein:
  each dotted line represents carbon atoms necessary to form a fused substituted or unsubstituted aromatic ring;
  n=1–18;
  m=1–18, selected independently from n;
  X and Y are selected independently from the group consisting of S, O, N, $CH_2$ and $C(CH_3)_2$;
  at least one of said $R_1$ and $R_2$ comprises a sulfonic acid or sulfonate group attached to the aromatic ring; and
  $R_3$ and $R_4$ are independently selected from the group consisting of carboxyl, activated carboxyl and methyl, wherein at least one of said $R_3$ and $R_4$ groups is carboxylate or activated carboxylate.

2. The activated cyclic-bridged dye of claim 1, wherein both $R_3$ and $R_4$ are carboxylates or activated carboxylates.

3. The activated cyclic-bridged dye of claim 1, wherein either $R_3$ or $R_4$ is carboxylate or activated carboxylate.

4. The activated cyclic-bridged dye of claim 1, wherein activated carboxylate is an ester.

5. The activated cyclic-bridged dye of claim 4, wherein said ester group is an ester of N-hydroxynapthalimide.

6. The activated cyclic-bridged dye of claim 1, wherein said aromatic ring is a phenyl, naphthyl or heterocyclic ring.

7. The activated cyclic-bridged dye of claim 1, wherein n=5.

8. The activated cyclic-bridged dye of claim 1, wherein m=1.

9. The activated cyclic-bridged dye of claim 1, wherein said dye is a cyanine dye.

10. The activated cyclic-bridged dye of claim 9, wherein said cyanine dye is selected from the group consisting of Cy7, BCy7, and DBCy7.

11. The activated cyclic-bridged dye of claim 1, wherein said dye is soluble in aqueous solutions.

12. A method of synthesizing a cyclic-bridged dye comprising the steps of:
(a) forming a cyclic-bridged derivative of the dye having a formula:

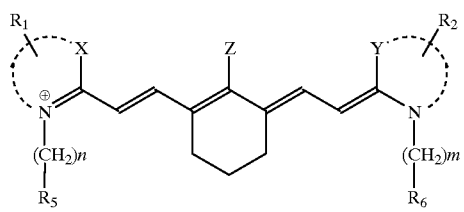

wherein:
each dotted line represents carbon atoms necessary to form a fused substituted or unsubstituted aromatic ring;
n=1–18;
m=1–18, selected independently from n;
X and Y are selected independently from the group consisting of S, O, N, $CH_2$ and $C(CH_3)_2$;
at least one of said $R_1$ and $R_2$ comprises a sulfonic acid or sulfonate group attached to the aromatic ring; and
$R_5$ and $R_6$ are independently selected from a carboxyl or a methyl, wherein at least one of said $R_5$ and $R_6$ is carboxyl; and
Z is a halogen;
(b) replacing the halogen with a hydrogen.

13. The method of claim 12, wherein both $R_5$ and $R_6$ are carboxyls.

14. The method of claim 12, wherein either $R_5$ or $R_6$ is carboxyl.

15. The method of claim 12, wherein said aromatic ring is a phenyl, naphthyl or heterocyclic ring.

16. The method of claim 12, wherein n=5.

17. The method of claim 12, wherein m=1.

18. The method of claim 12, wherein said dye is a cyanine dye.

19. The method of claim 12, wherein said cyanine dye is selected from the group consisting of Cy7, BCy7, and DBCy7.

20. The method of claim 12, wherein said halogen is a chlorine.

21. The method of claim 12, wherein the step of forming a cyclic-bridged derivative of the dye comprises:

(a1) mixing Compounds (XI) and (XII) with 2-chloro-1-formyl-3-hydroxymethylenc-cyclohexene to form a reaction mixture,
wherein Compound (XI) has a formula:

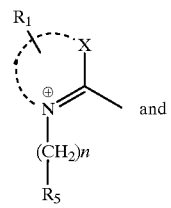

and

Compound (XII) has a formula:

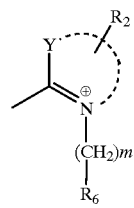

wherein:
each dotted line represents carbon atoms necessary to form a fused substituted or unsubstituted aromatic ring;
n=1–18;
m=1–18, selected independently from n;
X and Y are selected independently from the group consisting of S, O, N, $CH_2$ and $C(CH_3)_2$;
at least one of the $R_1$ and $R_2$ comprises a sulfonic acid or sulfonate group attached to the aromatic ring;
$R_5$ and $R_6$ are independently selected from a carboxyl or a methyl, wherein at least one of said $R_5$ and $R_6$ is carboxyl; and
(a2) maintaining the reaction mixture under conditions that allow the formation of the cyclic-bridged derivative of the dye.

22. The method of claim 21, wherein said aromatic ring is a phenyl, naphthyl or heterocyclic ring.

23. The method of claim 21, wherein n=5.

24. The method of claim 21, wherein m=1.

25. The method of claim 21, wherein the dye is cyclic Cy7, Compound (XI) is 1-(5-carboxypentyl)-1, 1, 2-trimethyl-(3H)-indolenium-7-sulfonate, and Compound (XII) is 3-ethyl-1, 1, 2-trimethyl-(3H)-indolenium-7-sulfonate.

26. The method of claim 21, wherein the dye is cyclic DBCy7, Compound (XI) is 1-(5-carboxypentyl)-1, 1, 2-trimethylbenz(e)indolenium-7-sulfonate, and Compound (XII) is 3-ethyl-1, 1, 2-trimethylbenz(e)indolenium-7-sulfonate.

27. The method of claim 21, wherein the step (a1) further comprises adding sodium acetate, dissolved in a combination of acetic acid and acetic anhydride, to the reaction mixture.

28. The method of claim 27, wherein the reaction mixture is heated under a condition that allows the formation of the cyclic-bridged derivative of the dye.

29. The method of claim 28, wherein the reaction mixture is heated to about 120° C. and is incubated for approximately one hour.

30. The method of claim 27, wherein a molar ratio between sodium acetate and the combination of acetitic acid and acetic anhydride is about 1:1.

31. The method of claim 27, wherein molar concentrations of Compounds (XI), (XII), 2-chloro-1-formyl-3-hydroxymethylene-cyclohexene, sodium acetate and the combination of acetic acid and acetic anhydride are equal.

32. The method of claim 12 further comprising:
reacting the cyclic-bridged dye with an activating reagent under a condition that allows the replacement of the hydrogen of the carboxyl with a reactive group, wherein the reactive group is capable of forming a covalent bond with a target molecule.

33. The method of claim 32, wherein the activated reagent is an ester of N-hydroxynapthalimide.

34. The method of claim 33, wherein said activating agent is N-hydroxynapthal-imide.

35. The method of claim 32, wherein said cyclic-bridged dye is dissolved in a solvent prior to reacting with the activating agent.

36. The method of claim 35, wherein the solvent is a DMF containing 1,1'-carbonyldiimidazole necessary for the activation reaction.

37. A method of labeling a biological or a non-biological material, comprising:
(a) providing a biological or a non-biological material having an amino group or a thiol group or a hydroxyl group;
(b) reacting the activated cyclic-bridged dye of claim 1 with the material under a condition sufficient to couple the dye to the material.

38. The method of claim 37, wherein said biological material is selected from the group consisting of proteins, cells, amino-modified nucleic acids, haptens, carbohydrates, dideoxynucleoside terminators, and combinations thereof.

39. The method of claim 38, wherein said biological materials are amino-modified oligonucleotides.

40. The method of claim 38, wherein said biological material is a dideoxynucleoside terminator.

* * * * *